United States Patent [19]

Jones

[11] Patent Number: 4,909,818
[45] Date of Patent: Mar. 20, 1990

[54] SYSTEM AND PROCESS FOR MAKING DIFFRACTIVE CONTACT

[76] Inventor: William F. Jones, 35 Benedict Rd., Pittsford, N.Y. 14534

[21] Appl. No.: 271,826

[22] Filed: Nov. 16, 1988

[51] Int. Cl.$^4$ ............................................. C03B 19/00
[52] U.S. Cl. .......................................... 65/31; 65/61; 219/121.68; 156/657; 351/160 R; 351/161
[58] Field of Search ............... 351/160 R, 161; 623/6; 65/31, 61; 156/658, 633, 657; 219/121.68

[56] References Cited

U.S. PATENT DOCUMENTS

| | | | |
|---|---|---|---|
| 4,476,154 | 10/1984 | Iesaka et al. | 156/657 |
| 4,563,565 | 1/1986 | Kampfer et al. | 351/160 R |
| 4,675,072 | 6/1987 | Bennett et al. | 156/657 |
| 4,704,016 | 11/1987 | de Carle | 351/161 |
| 4,797,316 | 1/1989 | Hecq et al. | 65/31 X |

OTHER PUBLICATIONS

PCT/US88/01651, May 17, 1988 filed, published 12/88, Portney et al.

Primary Examiner—Robert L. Lindsay
Attorney, Agent, or Firm—John S. Norton

[57] ABSTRACT

A diffractive bifocal eye lens, an otpical system, and processes for fabrication of such lenses are disclosed. The optical system includes the following principal elements in optical alignment along an optical axis, for accomplishing the indicated steps of the process: a laser for emission of ultraviolet light along the optical axis; a zone plate mask in the path of irradiation by the laser; and an imaging lens to project, with radiation from the laser, an image of the mask on the concave inner surface of an eye lens mounted coincident with the image surface of the optical system, thereby ablating the eye lens imagewise of the mask to generate a phase zone plate on the eye lens. The laser beam scans the zone plate mask to generate a composite image on the image surface. Alternatively, the phase zone plate is generated on the concave surface of a glass blank at the image surface to form a tool from which molds, and in turn lenses, are replicated. The light source is an argon fluoride excimer laser, emitting at 193 nm. The lens is a variable magnification lens to project various size images of the mask for producing zone plates of various powers as desired.

19 Claims, 4 Drawing Sheets

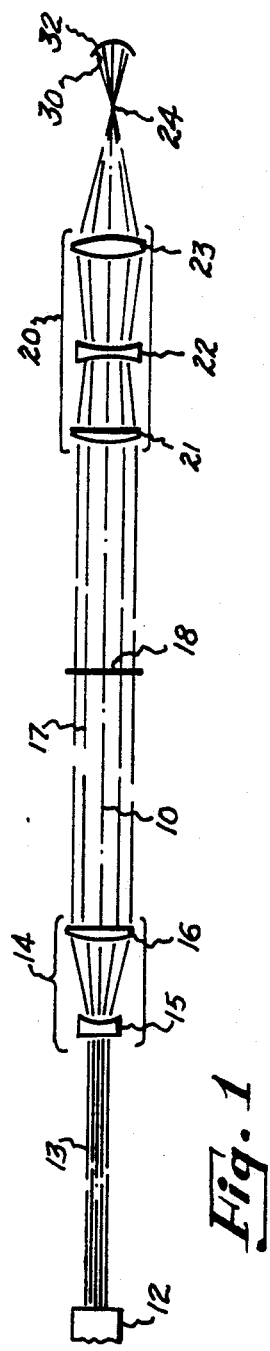
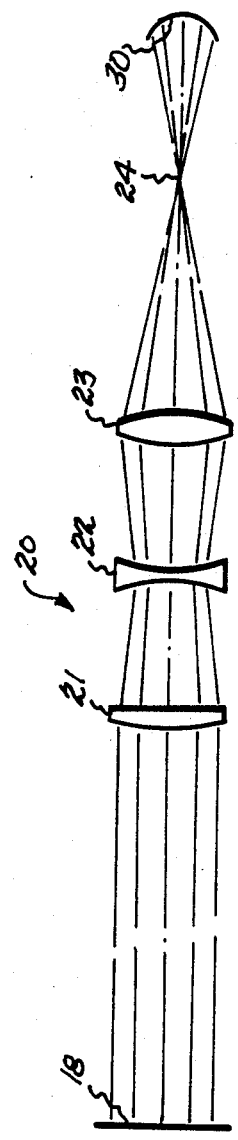
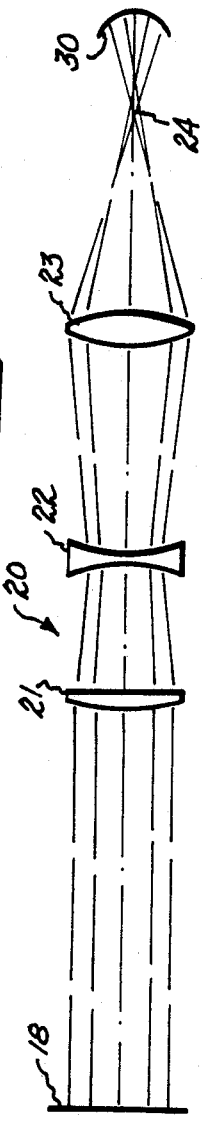

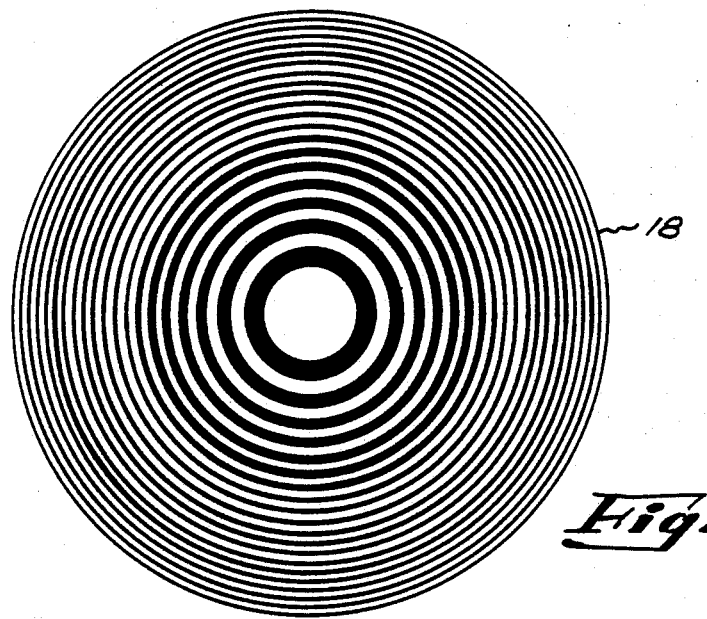
Fig. 4
Fig. 5
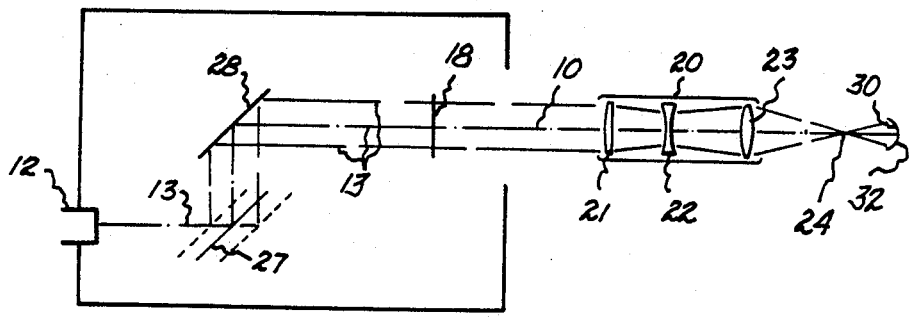

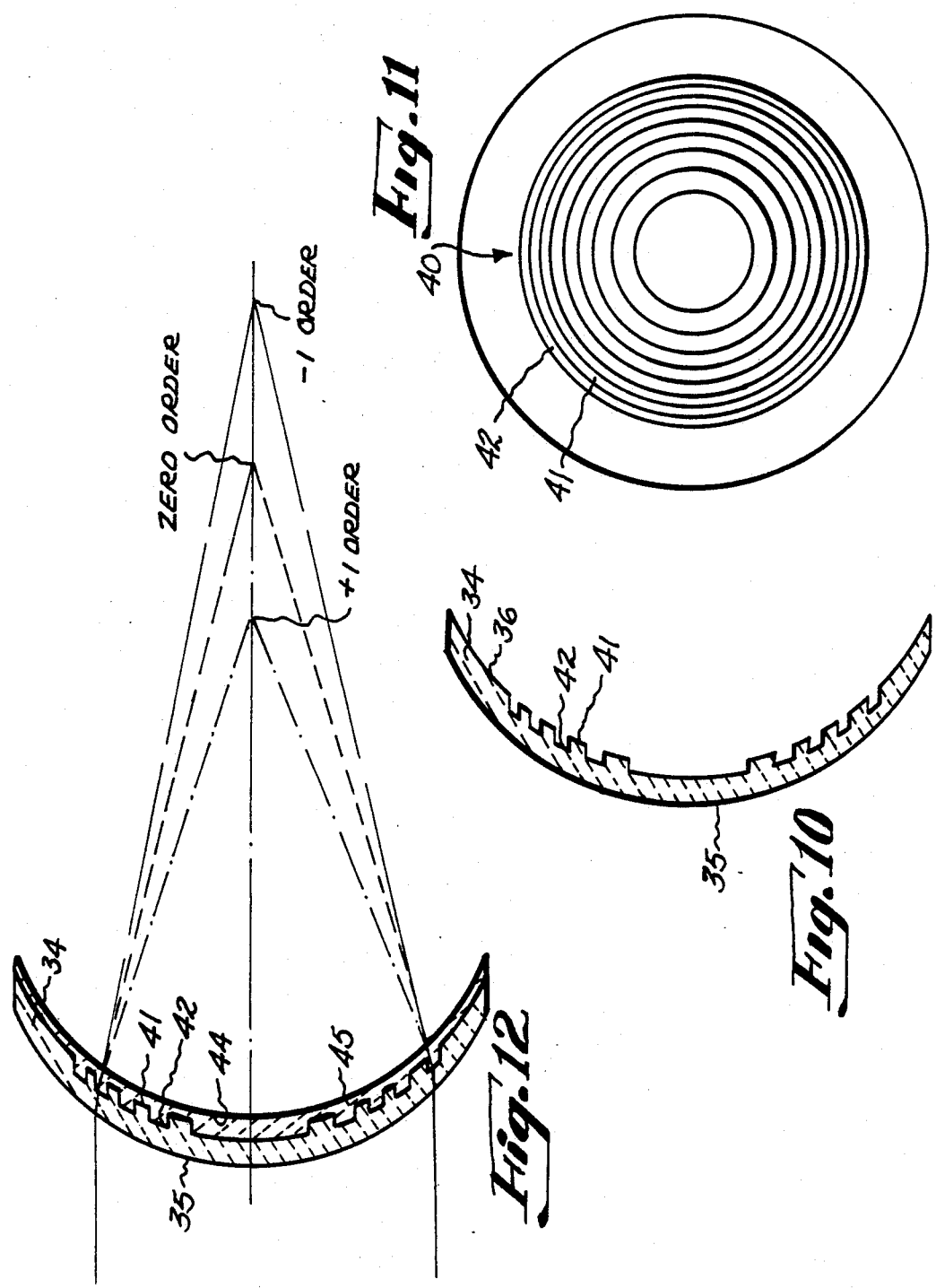

SYSTEM AND PROCESS FOR MAKING DIFFRACTIVE CONTACT

BACKGROUND OF THE INVENTION

1. Field of the Invention

The subject matter of this invention is contact lenses and intra-ocular lenses, and relates more particularly to a diffractive bifocal contact or intraocular lens and to a method of its manufacture by excimer laser ablation. In this specification, it will be convenient to use a single term to mean both "contact lens" and "intra-ocular lens". The term "eye lens" is hereby coined for this purpose.

2. Background Information

The adaptation of a phase zone plate for use as a diffractive bifocal contact lens was apparently first reported in 1966 by G. Forst in Der Augenoptiker. The lens was made by drawing the desired zone pattern on paper, producing a photographic negative of this pattern, projecting an image of the negative on an emulsion surface on the corneal bowl, and developing the photoemulsion. The Forst paper concludes that the feasibility of a diffractive bifocal contact lens, for special cases, is demonstrated. The fabrication of such a lens accurately, reproducibly, and in acceptable wearable form, has however remained a problem until the present.

U.S. Pat. No. 4,642,112 was issued on Feb. 10, 1987 to Michael H. Freeman. It discloses a contact lens having the appropriate curvatures providing basic refractive power for ordinary or distance vision; with a transmission hologram formed on the lens to provide diffractive power which is additive to the refractive power for near vision.

Generally, the etching of polymers by excimer lasers has been widely reported in the literature. Specifically, the production of diffraction gratings by laser etching of photo resists is also well known to the art.

Finally, European Patent Application No. 0,264,255 was published on Apr. 20, 1988 and discloses an excimer laser optical system for cutting and shaping contact lenses and like objects.

SUMMARY OF THE INVENTION

This invention includes a diffractive bifocal eye lens, and a unique optical system and processes for fast, accurate and reproducible fabrication of a such lenses. The optical system includes the following principal elements in optical alignment along an optical axis, for accomplishing the indicated steps of the process: a laser for emission of ultraviolet light along the optical axis; a zone plate mask in the path of irradiation by the laser; and an imaging lens to project, with radiation from the laser, an image of the mask on the concave inner surface of an eye lens mounted coincident with the image surface of the optical system, thereby ablating the eye lens imagewise of the mask to generate a phase zone plate on the eye lens. The laser beam scans the zone plate mask to generate a composite image on the image surface.

In an alternative method, the phase zone plate is generated on the concave surface of a glass blank at the image surface to form a tool from which molds, and in turn lenses, are replicated.

The preferred light source is an argon fluoride excimer laser, emitting at 193 nm. The preferred lens is a variable magnification lens to project various size images of the mask for producing zone plates of various powers as desired.

DRAWINGS

FIG. 1 is an optical diagram of a system according to this invention.

FIG. 2 is a partial diagram of the optical system at one magnification.

FIG. 3 is a partial diagram of the system at another magnification.

FIG. 4 is an enlarged axial view of a zone plate mask from FIG. 1.

FIG. 5 is an optical diagram of a modification of the system of FIG. 1.

FIG. 10 is an enlarged schematic cross section of a contact lens made according to this invention.

FIG. 11 is an axial view of the lens, as from the left of FIG. 6.

FIG. 12 is an optical schematic of the lens in use, showing ray traces of interest.

DESCRIPTION OF THE PREFERRED EMBODIMENT

Figure 9:
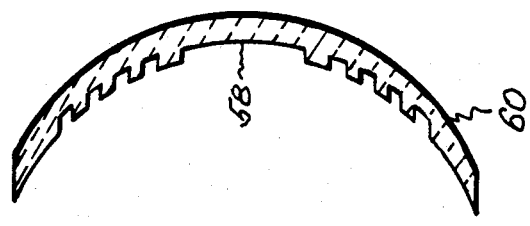
FIGS. 6–9 represent a sequence of steps in making lenses according to a modified system and process of this invention.
Figure 8:
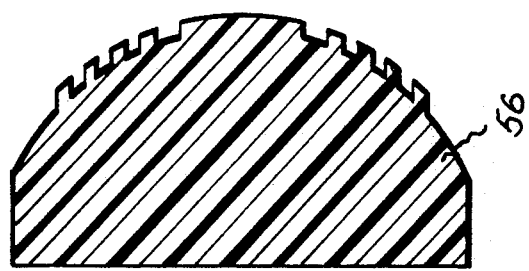

In FIG. 1, an optical system according to this invention is shown in optical alignment along an optical axis 10. The system includes an ultra violet laser 12, a beam profiler 14, a Fresnel zone plate mask 18, and an imaging lens system 20, all directed at an image surface 30 which is coincident with the concave inner surface of an eye lens or lens blank 32.

The ultra violet laser 12 is preferably an excimer laser, more specifically an Argon Fluoride laser, emitting at 193 nm, and capable of producing a sufficiently large output beam at intensities of from 100 to 600 $mJ/cm^2$. The output of laser 12 is a beam 13 of rectangular cross section.

The beam profiler 14 may include a negative cylindrical lens 15 to expand the rectangular output beam 13 in the direction shown in FIG. 1, and a positive cylindrical lens 16 to recollimate light from lens 15, thus to provide a profiled beam 17 of more uniform symmetrical intensity than the laser output beam 13. The profiled beam 17 traverses the zone plate mask 18. The imaging lens system 20 projects a reduced image of the pattern of mask 18 on the image surface 30.

The zone plate mask 18 (see also FIG. 4) may be simply a metal mask, apertured in accordance with the desired zone plate pattern. preferably, the zone plate mask 18 is formed on a substrate, coated with metal and photographically etched with alternate transparent and opaque annular rings in accordance with the desired zone plate pattern. A fused silica plate is preferred as the substrate because it is transmissive of ultraviolet light. Aluminum is the preferred coating metal because it reflects efficiently at the ultraviolet wavelengths of excimer lasers. A thin layer of chromium may be used between the substrate and the metal coating to improve adhesion. The entire surface may be coated with magnesium fluoride to protect the metal from oxidation and to reduce reflection losses from the substrate.

In its simplest form, the imaging lens 20 may be a single lens of fixed magnification. Preferably, however, lens system 20 is a variable magnification or zoom lens system, providing a variable reduction of the mask image at the image surface 30, and consequently various diffractive powers of the phase zone plate generated at the image surface 30. As an example, zoom lens system 20 includes lens elements 21, 22, and 23, one or more of which may be movable relative to the others in many known configurations.

FIGS. 2 and 3 are partial diagrams of the optical system, each at a different magnification. The lens system 20 in FIG. 2 may be set at a magnification of 2.63 X. The same lens system 20 in FIG. 3 may be at a magnification of 3.03 X. These are, of course, only exemplary figures. It is intended that the zoom lens system 20 will be used at many different magnifications within its useful range. The focal point of lens system 20 is represented at 24.

As shown in FIGS. 1, 2, and 3, the zone plate mask 18, which is the object of this optical system, is flat. Its image surface 30 is curved. This is purposeful. The lens system 20 is designed to provide this curvature of field, comparable to the inner curvature of a contact lens blank. The contact lens blank 32 is positioned so that its concave inner surface coincides with the curved image surface 30. A sharp image of the flat zone plate mask 18 is thus formed on the concave lens blank 32, coinciding as it does with the image surface 30.

Another requirement and purpose of the optical system is to prevent ionization of air at the system focal point. If the lens system 20 were such that incident parallel light were brought to an infinitesimal point focus at the lens focal point 24, resulting local ionization of air at the focal point may have undesirable effects on the operation of the system, the quality of the image formed, and so on. This is avoided by deliberately providing spherical aberration in the lens design. The practical focal point of the lens system is thus not infinitesimal.

Operation of the system is as follows. The image of the zone plate mask 18 is projected on the concave inner surface of a contact lens blank 32 at the image surface 30, ablating or etching that surface imagewise of the mask 18. The process is carried out in a number of pulses of the laser, as many as ten for example, rather than in a single discharge. The desired total depth of etch is about 3 microns, the exact depth depending on the refractive index of the lens material. The depth of etch per pulse of the laser is typically less than 1 micron. By controlling the number of pulses, the depth of etch can be very closely controlled to produce the desired constant optical path difference of one half wavelength across each boundary of each zone of the phase zone plate generated on the lens blank. This operation provides a non-contact optical means, rather than mechanical cutting, to generate a phase zone plate on a contact lens.

FIG. 1 represents the basics of the system of this invention. A preferred modification of this basic system is represented in FIG. 5. The system of FIG. 5 has much in common with that of FIG. 1, and common elements are similarly numbered. As in FIG. 1, the output beam 13 is a rectangular strip of light in cross section. Instead of a beam profiler 14 as in FIG. 1 to give the beam more area, the rectangular output beam 13 is caused to scan the Fresnel zone plate mask 18. A movable mirror 27 and a stationary mirror 28 are positioned as shown, both at 45° to the optical axis 10. The movable mirror thus deflects the optical axis 90° onto the stationary mirror, which in turn deflects the optical axis 90° onto the Fresnel zone plate mask 18 and through the optics to the image surface 30. The movable mirror 27 is reciprocable from one extreme position 1, through a center position 2, to the other extreme position 3, and back. Through one such stroke, from position 1 to position 3, the output beam 13 scans the Fresnel zone plate mask 18 from bottom (line 1) to top (line 3) as represented on the drawing. Scanning operation, according to the system of FIG. 5, enables increased energy concentration at the target for better results.

In the system thus far described, the workpiece is a contact lens blank 32, and the finished product of the process is a lens with a phase zone plate generated on its inner surface. The system and process are also intended to produce tools from which many molds will be made, and from these molds many more lenses will in turn be made.

Figure 7:
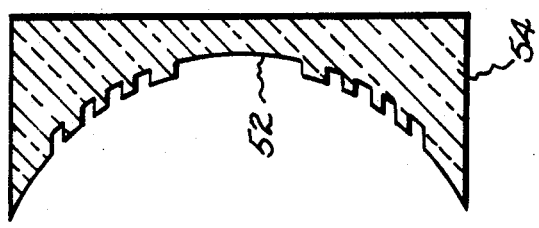
Figure 6:
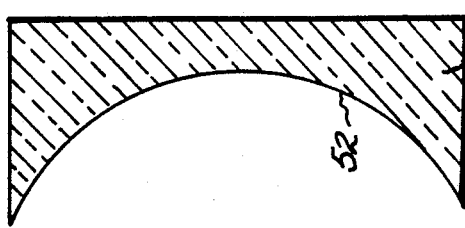

Reference is now to FIGS. 6-9, representing a sequence of steps in making tools, molds, and lenses. In this mode, the workpiece is a glass tool blank 50 (FIG. 6), having a concave surface 52 to be positioned coincident with the image surface 30 of FIG. 1 or FIG. 5. A positive pattern of the desired phase zone plate is formed and etched on the concave glass surface 52 to produce a glass tool 54 (FIG. 7). Plastic molds 56 (FIG. 8) are then made from the glass tool 54, such molds being negatives of the tool 54 and of the desired lens. A mold 56 thus formed is then used to replicate the phase zone plate on the concave inner surface 58 of a contact lens 60.

Whether the system and process are used to make lenses directly, or to make tools from which molds and then lenses are in turn made, the variable magnification of the optics enables production of a theoretically limitless number of different zone plate profiles, i.e. bifocal additions.

FIGS. 10 and 11 show schematically, and substantially enlarged, a contact lens 34 made from a lens blank by the system and process of this invention. Lens 34 includes a front surface 35 and a rear surface 36. A phase zone plate 40 is made up of a number of concentric phase zones 41, 42 on the rear or inside surface 36 of the lens. The several zones are of equal area, their radii being related according to the series: $R_1 = 1$; $R_2 = R_1 \sqrt{2}$; $R_3 = R_1 \sqrt{3}$; $R_4 = R_1 \sqrt{4}$; and so on. In FIG. 10, zones 42 are seen to be grooves of uniform depth in the concave lens surface 36. The depth of these grooves is calculated from the refractive index difference, which will be present in the lens on the eye at this interface to produce an effective optical path difference of 0.280 microns at each discontinuity. Typically, this physical profile depth will be several microns, but may be tens of microns or more. The grooves 42 are preferably on the rear surface 36 of the lens, as shown, so as to be filled with tears while the lens is on the eye. The correct depth for the lens/tear combination depends on lens material, i.e. refractive index, but is typically about 3 microns. The grooves shown are, of course, greatly exaggerated; a cross section of the actual contact lens will appear perfectly continuous.

Another form of the contact lens is a composite lens in which the generated phase zone plate is sandwiched between two lens materials of different refractive index, or within the body of a single lens material. The outer surfaces of such a configuration are perfectly smooth and continuous, in fact as well as in appearance, and the zones themselves less conspicuous. The optical principle of the lens in this form is the same as that of the lens in FIG. 10.

FIG. 12 illustrates the optical action of the contact lens 34. The lens 34, with the phase zone plate 40 on its inner surface, is shown on a corneal surface 44. there is a film of tear fluid 45 between the cornea 44 and the lens inner surface. Light entering the lens 34 is diffracted by the zone plate 40 away from the normal refractive focus of the lens (indicated as the "zero order" image).

At the design wavelength, and with a perfect profile, theory predicts that complete destructive interference occurs at the zero order and at all even orders if the phase shift is exactly half of the design wavelength at each discontinuity. At the odd orders, theory predicts that about 41% of the input light is expected in the +1 order and 41% in the −1 order, with less than 5% occurring in any higher order. Errors in the profile depth within 20% will alter the intensity of light in each order only slightly. The lens performance will therefore be very tolerant of production variability with respect to profile depth.

The system and process have so far been described and illustrated with reference to contact lenses and contact lens manufacture. The invention is also intended for the manufacture of intra-ocular lenses. Intra-ocular lenses are lenses implanted in the eye of a patient after cataract surgery to replace the normal crystalline lens. Intra-ocular lenses do not change shape, of course, for distance accomodation, and patients can see clearly at one distance only. An intra-ocular lens with a bifocal addition according to this invention will allow such a patient both near and distance imagery.

The foregoing description of this invention is intended as illustrative. The concept and scope of the invention are limited only by the following claims and equivalents thereof.

In the following claims, as in the specification, the term "eye lens" is used as inclusive of "contact lens" and "intra-ocular lens".

What is claimed is:

1. An optical system for making a diffractive eye lens, including, disposed in optical alignment along an optical axis:
   a laser for emission of ultraviolet light along said optical axis;
   a zone plate mask disposed for irradiation by said laser; and
   an imaging lens to project an image of said mask on a concave curved image surface coincident with the inner concave surface of an eye lens.

2. An optical system as defined in claim 1, in which said imaging lens is a variable magnification lens to project various size images of said mask on said image surface.

3. An optical system as defined in claim 1 in which said laser is an excimer laser.

4. An optical system as defined in claim 3 in which said laser is an argon fluoride laser emitting at 193 nm.

5. An optical system as defined in claim 1, further including means to scan said zone plate mask by said emission from said laser to generate a composite image of said mask on said image surface.

6. A process of making a diffractive eye lens, including the following steps:
   a. mounting an eye lens with the concave surface thereof coincident with the image surface of a projection optical system; and
   b. with radiation from an ultraviolet laser, projecting an image of a zone plate mask on said image surface, thereby ablating said lens imagewise of said mask to generate a zone plate on said lens.

7. A process as defined in claim 6, further including the step of:
   c. varying the magnification of said optical system to thereby vary the power of the zone plate generated on the next lens so made.

8. A process as define din claim 6, further including the step of:
   c. scanning said zone plate mask by said emission from said laser to generate a composite image of said mask on said image surface.

9. An optical system for generating a phase zone plate on a tool from which to replicate a diffractive eye lens, including, disposed in optical alignment along an optical axis:
   a laser for emission of ultraviolet light along said optical axis;
   a zone plate mask disposed for irradiation by said laser; and
   an imaging lens to project an image of said mask on a concave curved image surface coincident with a concave surface of said tool.

10. An optical system as defined in claim 9 in which said tool is of glass.

11. An optical system as defined in claim 9, in which said imaging lens is a variable magnification lens to project various size images of said mask on said image surface.

12. An optical system as defined in claim 9 in which said laser is an excimer laser.

13. An optical system as defined in claim 12 in which said laser is an argon fluoride laser emitting at 193 nm.

14. An optical system as defined in claim 9, further including means to scan said zone plate mask by said emission from said laser to generate a composite image of said mask on said image surface.

15. A process of making a tool for replicating diffractive eye lenses, including the following steps:
   a. mounting a concave tool with the concave surface thereof coincident with the image surface of a projection optical system; and
   b. with radiation from an ultraviolet laser, projecting an image of a zone plate mask on said image surface, thereby ablating said concave tool imagewise of said mask.

16. A process as defined in claim 15 in which said tool is of glass.

17. A process as defined in claim 15, further including the step of:
   c. replicating a convex mold from said concave tool.

18. A process as defined in claim 17, further including the step of:
   d. replicating an eye lens from said convex mold.

19. A process as defined in claim 15, further including the step of:
   c. varying the magnification of said optical system to thereby vary the power of the zone plate mask image and of lenses derived therefrom.

* * * * *

UNITED STATES PATENT AND TRADEMARK OFFICE
CERTIFICATE OF CORRECTION

PATENT NO. : 4,909,818
DATED : March 20, 1990
INVENTOR(S) : William F. Jones

It is certified that error appears in the above-identified patent and that said Letters Patent is hereby corrected as shown below:

On the first page of the patent, in the title, please insert the word --Lenses-- after "Contact".

Before the heading (21) Appln. No.: 271,826, please insert the heading (73) Assignee: Bausch & Lomb Incorporated
 Rochester, N.Y.

In the Abstract, line 1, delete "otpical" and insert therefore --optical--.

Col. 1, in the title, please insert the word --Lenses-- after "Contact".

Col. 4, line 43, after "$R_3=R_1$" delete "29" and substitute therefor --$\sqrt{}$--.

Signed and Sealed this

Twenty-second Day of October, 1991

Attest:

HARRY F. MANBECK, JR.

Attesting Officer

Commissioner of Patents and Trademarks